United States Patent [19]

Hamill et al.

[11] Patent Number: 5,391,492
[45] Date of Patent: Feb. 21, 1995

[54] A83850 ANTIBIOTICS

[75] Inventors: Robert L. Hamill, Greenwood; Raymond C. Yao, Carmel, both of Ind.

[73] Assignee: Eli Lilly and Company, Indianapolis, Ind.

[21] Appl. No.: 66,352

[22] Filed: May 21, 1993

Related U.S. Application Data

[62] Division of Ser. No. 924,137, Aug. 3, 1992, abandoned, which is a division of Ser. No. 568,578, Aug. 16, 1990, Pat. No. 5,187,082.

[51] Int. Cl.$^6$ .......................... C12N 1/12; C12N 1/20
[52] U.S. Cl. ................... 435/252.1; 435/71.3; 435/170
[58] Field of Search ............... 435/252.1, 71.3, 170

[56] References Cited

U.S. PATENT DOCUMENTS

| | | | |
|---|---|---|---|
| 4,495,179 | 1/1985 | Hoehn et al. | 514/9 |
| 4,547,488 | 10/1985 | Merkel | 514/10 |
| 4,548,924 | 10/1985 | Michel | 514/10 |
| 4,548,925 | 10/1985 | Higgins et al. | 514/10 |
| 4,552,701 | 11/1985 | Nagarajan et al. | 260/112.5 |
| 4,558,008 | 12/1985 | Boeck et al. | 435/75 |

OTHER PUBLICATIONS

Harris, C. M., et al., *J. Am. Chem. Soc.*, 105 No. 23: 6915–6922 (1983).
Lechevalier, M. P. et al., *Int. J. Syst. Bacteriol.*, 36, No. 1: 29–37 (1986).
Hessen, A. et al., *Int. J. Syst. Bacteriol.*, 37, No. 3: 292–295 (1987).

*Primary Examiner*—Douglas W. Robinson
*Assistant Examiner*—Maria Luisa Osoteo
*Attorney, Agent, or Firm*—Steven A. Fontana; Gerald V. Dahling

[57] ABSTRACT

New glycopeptide antibiotic A83850, comprising A83850A, and A83850B, is produced by *Amycolatopsis albus* strain NRRL 18532. A83850A and A83850B can be reduced to give new biologically active denatures. The A83850 antibiotics have activity against Gram-positive bacteria comparable to that of vancomycin.

1 Claim, 4 Drawing Sheets

A83850 ANTIBIOTICS

This application is a division of application Ser. No. 07/924,137, filed Aug. 3, 1992, now abandoned, which is a division of application Ser. No. 07/568,578, filed Aug. 16, 1990, (U.S. Pat. No. 5,187,082).

SUMMARY OF THE INVENTION

This invention relates to antibiotic A83850 comprising individual components A83850A and A83850B, to their reduced forms, and to their salts. It also relates to a process for producing antibiotic A83850 by cultivating a member of a newly described species of the genus Amycolatopsis, *Amycolatopsis albus* sp. nov., selected from *A. albus* strain NRRL 18532, or an A83850-producing mutant thereof, under submerged aerobic fermentation conditions and to a process for preparing the reduced forms of A83850 A and B.

The A83850 antibiotics inhibit the growth of certain pathogenic microorganisms, particularly Gram-positive microorganisms. The A83850 antibiotics also promote growth and improve feed efficiency in animals and improve milk production in ruminant animals. Thus, the use of A83850 antibiotics for these purposes is also part of this invention.

This invention also relates to biologically-purified cultures of the *Amycolatopsis albus* strain NRRL 18532, which are useful for producing the A83850 antibiotics.

DESCRIPTION OF THE DRAWINGS

Infrared absorption spectra of the A83850 components are shown in FIGS. 1-2 as follows.

DETAILED DESCRIPTION OF THE INVENTION

Although many beneficial antibiotics are available today, the need to find improved antibiotics for human medicine continues. For example, vancomycin is a commercially successful antibiotic which has saved many lives. Recently, vancomycin has become less effective against enterococci because of resistance development. Antibiotics which have an activity like that of vancomycin but which have improved pharmacokinetic properties or are active against vancomycin resistant enterococci are in demand.

This invention relates to an antibiotic which is structurally similar to vancomycin. In particular, this invention relates to the new antibiotic A83850 comprising individual components A83850A and A83850B. Further aspects of this invention are the individual A 83850 components and their salts, especially their pharmaceutically acceptable salts, and the reduced forms of the A83850 components.

Antibiotic A83850 is produced by culturing a strain of the novel microorganism *Amycolatopsis albus* NRRL 18532, or an A83850-producing mutant thereof. As those skilled in fermentation processes will recognize, the ratio of the components in antibiotic A83850 will vary, depending upon the fermentation conditions used to produce it. A83850A and A83850B are separated and isolated as individual compounds, as described infra.

In discussions of utility, the term "A83850 antibiotic" will denote a member selected from the group consisting of antibiotic A83850, A83850A, and A83850B, reduced A83850A and A83850B, and their pharmaceutically acceptable salts.

A83850 is soluble in water, dilute aqueous acid, dilute aqueous base and in mixtures of water and solvents such as methanol, ethanol, dimethylformamide, dimethyl sulfoxide, acetonitrile and acetone and other polar solvents.

The following paragraphs describe the physical and spectral properties of the A83850 components which have thus far been characterized.

A83850A

Figure 1:
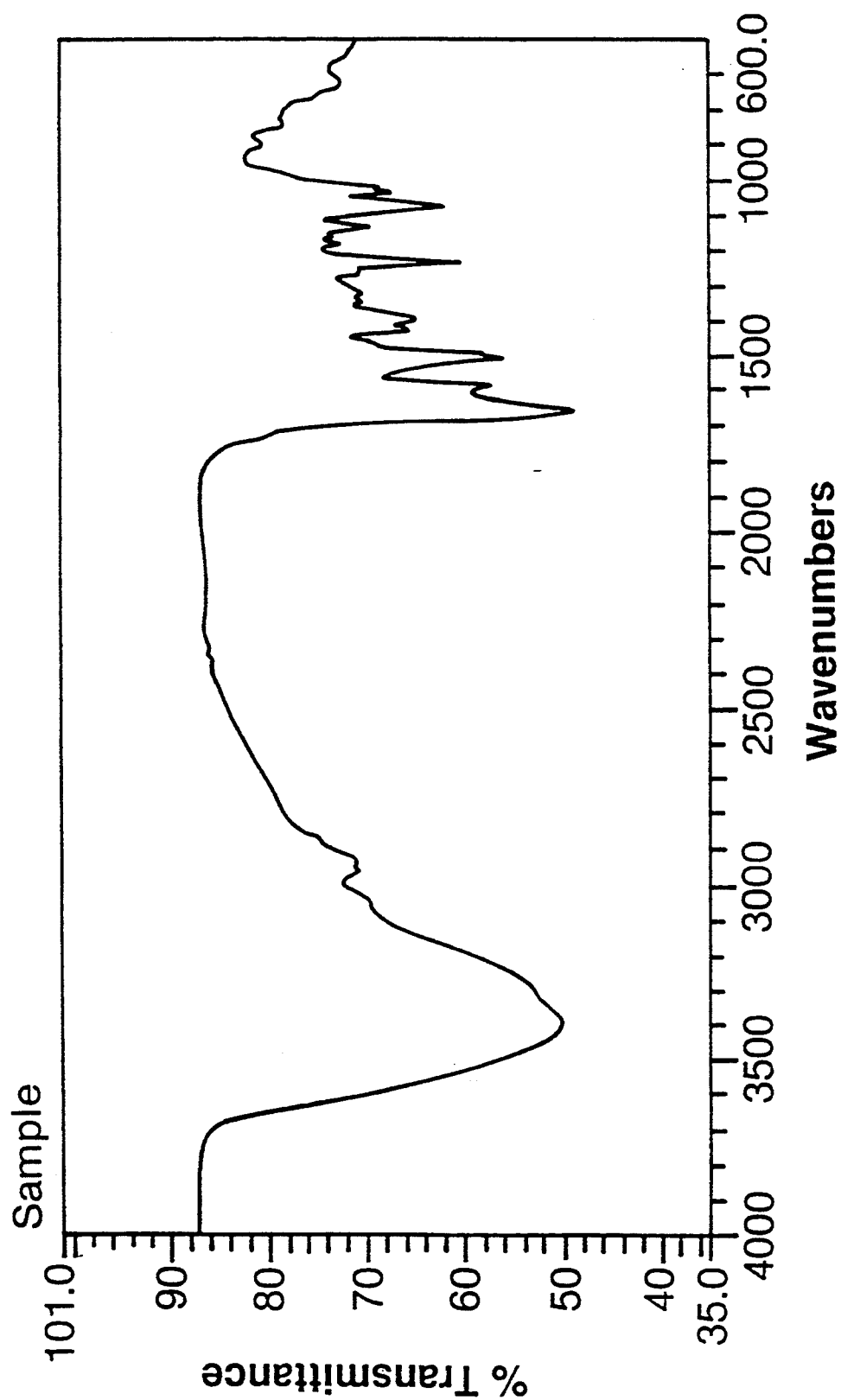
FIG. 1—A83850A (in KBr disk)
FIG. 2—A83850B (in KBr disk)

A83850A has the following characteristics:
Molecular Weight: 1459
Molecular Formula: $C_{67}H_{75}N_9O_{24}Cl_2$
FAB-MS (thioglycerol) (M+1) Found: 1460.6
UV ($H_2O$) λmax: 279 nm (ε 6170)
IR (KBr): 3401, 2961, 2936, 1656, 1589, 1506, 1425, 1396, 1333, 1314, 1232, 1177, 1157, 1130, 1063, 1028, 1017, 895, 844, and 721 (see FIG. 1)
NMR [$(CD_3)_2SO$]: see Table I
pKa ($H_2O$): 3.1, 6.8, 8.2, 9.0)

A83850B

Figure 2:
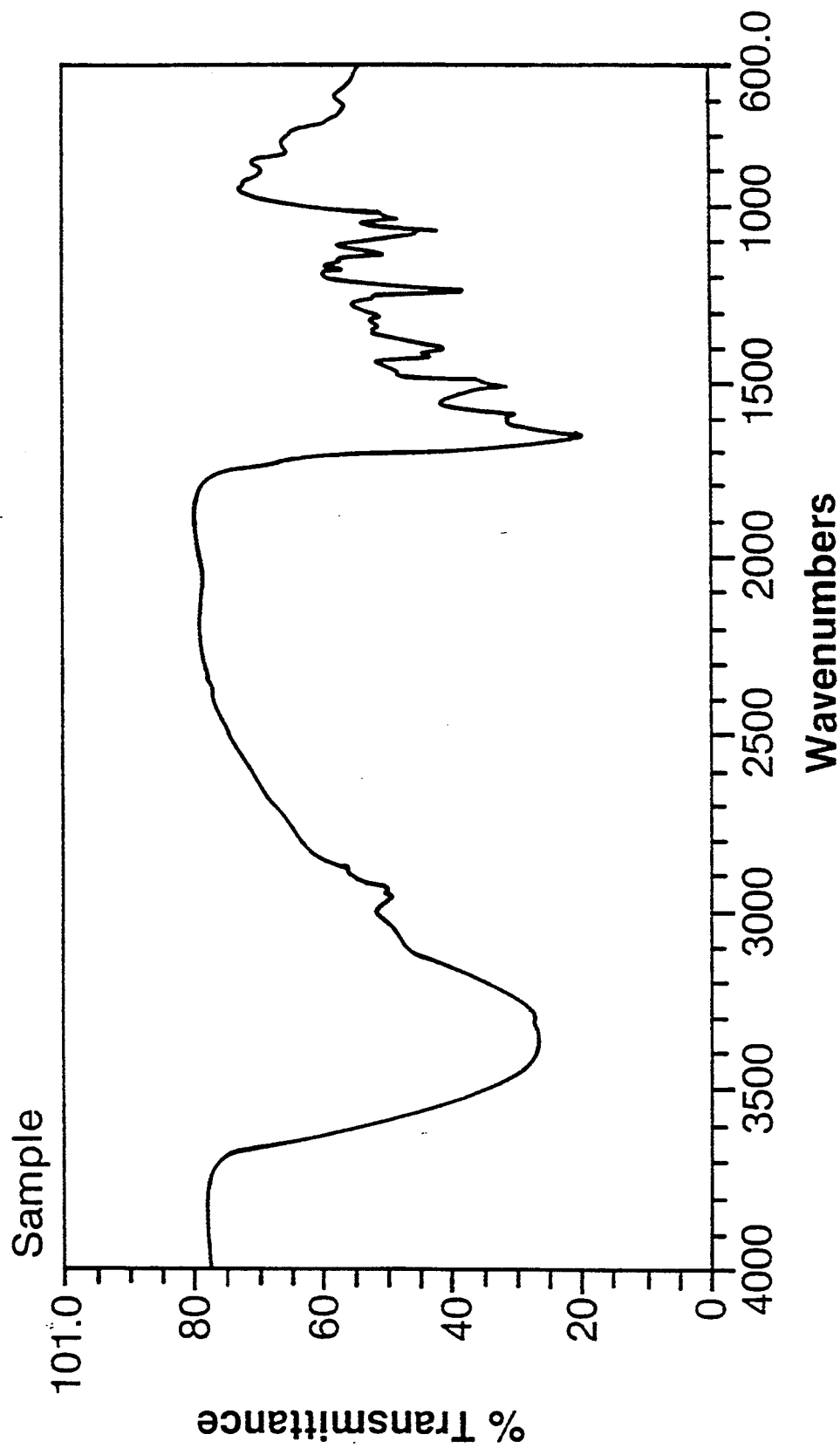

A83850B has the following characteristics:
Molecular Weight: 1445
Molecular Formula: $C_{66}H_{73}N_9O_{24}Cl_2$
FAB-MS (thioglycerol) (M+1) Found: 1446.4
UV ($H_2O$) λmax: 279 run (ε 6720)
IR (KBr): 3386, 2962, 2937, 1654, 1589, 1507, 1423, 1397, 1339, 1312, 1232, 1177, 1156, 1131, 1064, 1029, 894, 845, 717 and 635 (see FIG. 2)
NMR [$(CD_3)_2SO$]: see Table II
pKa ($H_2O$): 3.6, 7.1, 8.5, 10.0

Nuclear magnetic resonance spectra were recorded for A83850A and A83850B at 60° C. on a Bruker AM500 spectrometer. The solvent in each case was dimethyl sulfoxide-$d_6$ (DMSO-$d_6$) plus a trace amount of trifluoroacetic acid. The data from these spectra are compared with similar data for vancomycin (60° C. in DMSO) and are listed in Table I.

TABLE I

| Nuclear Magnetic Resonance Data of A83850A, A83850B and Vancomycin $^1$H Chemical Shifts (TMS = 0.0) | | | |
|---|---|---|---|
| Assignment | A83850A | A83850B | Vancomycin |
| A—NH | 6.52 | 6.53 | 6.65 |
| A2' | 4.18 | 4.17 | 4.15 |
| A1' | 5.13 | 5.13 | 5.13 |
| A2 | 7.81 | 7.81 | 7.88 |
| A5 | 7.33 | 7.34 | 7.30 |
| A6 | 7.46 | 7.47 | 7.44 |
| B—NH | 8.30 | 8.31 | 7.98 |
| B1' | 5.75 | 5.78 | 5.70 |
| B2 | 5.67 | 5.65 | 5.49 |
| B6 | 5.20 | 5.19 | 5.24 |
| C—NH | 8.63 | 8.48 | 7.92 |
| C2' | 4.92 | 4.92 | 4.84 |
| C1' | 5.20 | 5.19 | 5.24 |
| C2 | 7.54 | 7.56 | 7.50 |
| C3 | 7.20 | 7.19 | 7.24 |
| C6 | 7.54 | 7.49 | 7.28 |
| D—NH | 8.42 | 8.42 | 8.10 |
| D1' | 4.48 | 4.47 | 4.27 |
| D2 | 6.29 | 6.29 | 6.25 |
| D4 | 6.40 | 6.40 | 6.57 |

TABLE I-continued
Nuclear Magnetic Resonance Data of A83850A,
A83850B and Vancomycin
$^1$H Chemical Shifts (TMS = 0.0)

| Assignment | A83850A | A83850B | Vancomycin |
|---|---|---|---|
| E—NH | 8.57 | 8.54 | 8.48 |
| E1' | 4.46 | 4.47 | 4.44 |
| E2 | 7.16 | 7.16 | 7.21 |
| E5 | 6.71 | 6.71 | 6.71 |
| E6 | 6.79 | 6.78 | 6.74 |
| Asn—NH | 6.35 | 6.43 | 6.56 |
| α | 4.22 | 4.24 | 4.33 |
| β | 2.68, 2.17 | 2.60, 2.17 | 2.51, 2.14 |
| NH$_2$ | 7.36, 6.93 | not assigned | 7.26, 6.78 |
| Leu—NXCH$_3$ | 2.89 (X=CH$_3$)[1] | 2.64 (X=H) | 2.34 (X=H)[2] |
| α | 4.07 | 3.98 | 3.27 |
| β | 1.84, 1.62 | 1.69, 1.60 | 1.56, 1.46 |
| γ | 1.56 | 1.68 | 1.74 |
| δ | 0.94, 0.88 | 0.92, 0.88 | 0.91, 0.87 |
| Glucose #1 | 5.38 | 5.38 | 5.33 |
| #2 | 3.67 | 3.67 | 3.59 |
| #3 | 3.56 | 3.58 | 3.48 |
| #4 | 3.34 | 3.34 | 3.29 |
| #5 | 3.34 | 3.34 | not assigned |
| #6 | 3.72, 3.58 | 3.72, 3.58 | 3.70, 3.56 |
| Vancosamine #1 | 5.48 | 5.47 | 5.29 |
| #2 | 2.52, 2.37 | 2.46, 2.37 | 1.92, 1.76 |
| #3(CH$_3$) | 1.50 | 1.50 | 1.35 |
| #4 | —[3] | — | not assigned |
| #5 | 5.51 | 5.51 | 4.66 |
| #6 | 1.16 | 1.15 | 1.08 |

[1] —N(CH$_3$)$_2$ = 41.06 ppm ($^{13}$C)
[2] —NH(CH$_3$) = 30.90 ppm ($^{13}$C)
[3] >C=O = 212.23 ppm ($^{13}$C)

Thus, comparative NMR studies indicated that the A83850 components differ from vancomycin in that they each contain the amino sugar 4-keto vancosamine instead of vancosamine. A83850A also contains an additional methyl group at the N-terminus of the N-methyl leucine group.

A83850 and its individual components A83850A and A83850B can be reduced, using mild reduction procedures understood in the art, such as sodium cyanoborohydride, sodium borohydride or selective hydrogenation, to yield compounds containing a reduced amino sugar.

The $^1$H NMR assignments for the amino sugar in reduced A83850A and reduced A83850B (DMSO-d$_6$; 60° C.) are shown in Table II.

TABLE II
Nuclear Magnetic Resonance Data of Amino Sugar in Reduced Factors

| | $^1$H Parameters, δ(J) | |
|---|---|---|
| Assignment | A83850A | A83850B |
| 1 | 5.34 | 5.34 |
| 2 | 1.87, 1.65 | 1.87, 1.65 |
| 3(CH$_3$) | 1.22 | 1.22 |
| 4 | 3.00 (J = 9½ H$_z$) | 3.00 (J = 9½ H$_z$) |
| 5 | 4.16 | 4.16 |
| 6 | 1.10 | 1.10 |

These data indicate that the reduced forms of the A83850 components each contain the amino sugar 4-epi-vancosamine (3-methyl-acosamine).

Furthermore, the fast atom bombardment mass spectra of reduced A83850A showed (M+1)=1462, and reduced A83850B showed (M+1)=1448. These two additional mass units in the reduced antibiotics is consistent with the reduction of a carbonyl group to the hydroxy group.

Thus, the A83850 components constitute a new family of glycopeptides which clearly resemble the vancomycin molecule in general structure but contain a modified vancosamine.

Therefore, the compounds of this invention have the structure shown in Formula (1):

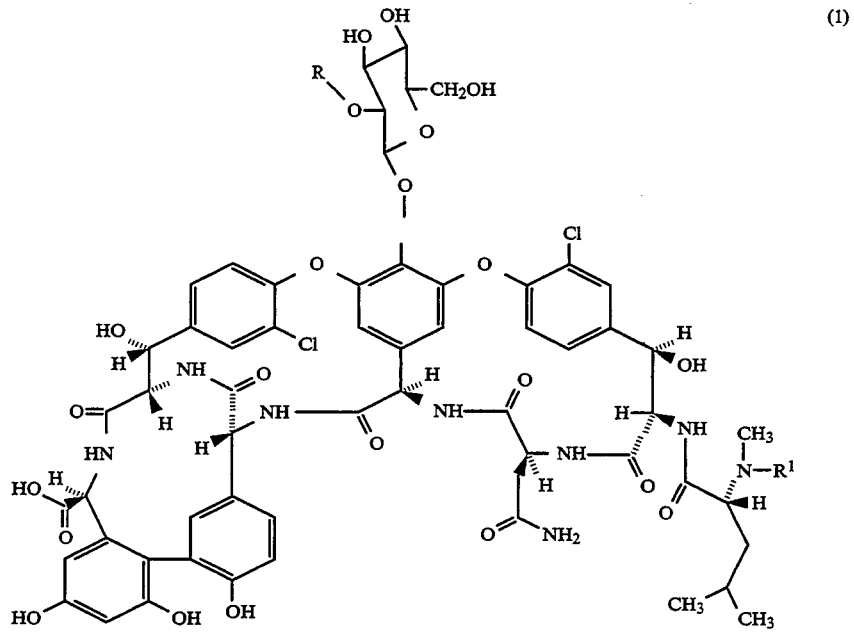

wherein R is a group selected from

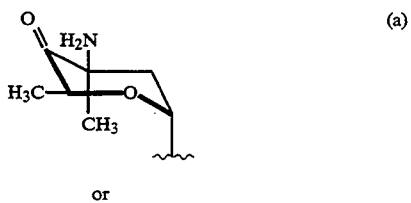

or

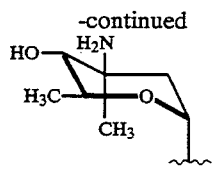

(b)

and R[1] is hydrogen or methyl; or a salt thereof.

Thus, the A83850 components and the reduced A83850 components have the following individual structures:

| A83850 Compound | R | R[1] |
| --- | --- | --- |
| A83850A | (a) | $CH_3$ |
| A83850B | (a) | H |
| reduced A83850A | (b) | $CH_3$ |
| reduced A83850B | (b) | H |

A83850 and its individual components A83850A A83850B can react to form various salts. All such forms of these antibiotics are part of this invention. A83850 salts are useful, for example, for separating and purifying A83850. In addition, the salts have an improved solubility in water.

A83850 salts are prepared using standard procedures for salt preparation. For example, A83850 can be neutralized with an appropriate acid to form an acid addition salt.

The acid addition salts are particularly useful. Representative suitable salts include those salts formed by standard reactions with both organic and inorganic acids such as, for example, sulfuric, hydrochloric, phosphoric, acetic, succinic, citric, lactic, maleic, fumaric, cholic, pamoic, mucic, D-glutamic, d-camphoric, glutaric, glycolic, phthalic, tartaric, formic, lauric, stearic, salicylic, methanesulfonic, benzenesulfonic, sorbic, picric, benzoic, cinnamic and like acids.

Pharmaceutically acceptable acid addition salts are an especially preferred group of salts of this invention.

Antibiotic A83850 is produced by culturing an A83850-producing strain of *Amycolatopsis albus* under submerged aerobic conditions in a suitable culture medium until substantial antibiotic activity is produced. The antibiotic can be recovered using various isolation and purification procedures understood in the art.

This invention also relates to a biologically-purified culture of a microorganism selected from *Amycolatopsis albus* NRRL 18532, or an A83850-producing mutant thereof. These microorganisms are useful because they produce antibiotic A83850. For convenience in the discussion which follows, the NRRL 18532 strain has been designated culture A83850.

Culture A83850 was isolated from a soil sample. It has been deposited and made part of the culture collection of the Midwest Area Northern Regional Research Center, Agricultural Research Service, United States Department of Agriculture, 1815 North University Street, Peoria, Ill., 61604, from which it is available to the public under the accession number NRRL 18532.

Taxonomic studies of culture A83850 were carried out by Frederick P. Mertz of the Lilly Research Laboratories. Based on these studies, the microorganism is classified as a new species of the genus Amycolatopsis, which has been named *Amycolatopsis albus* sp. nov. This classification is based on direct laboratory comparisons and examination of published descriptions of similar species. [A. Henssen, H. W. Kothe, and R. M. Kroppenstedt, "Transfer of *Pseudonocardia azurea* and *Pseudonocardia fastidiosa*" to the genus Amycolatopsis, with emended species descriptions", *Int. J. Syst. Bacteriol.* 37, 292–295 (1987); M. P. Lechevalier, M. P., H. Prauser, D. P. Labeda, and J. S. Ruan, "Two new genera of nocardioform actinomycetes: Amycolata gen. nov. and Amycolatopsis gen. nov.", *Int. J. Syst. Bacteriol.* 36, 29–37 (1986)]

Methods Used

The methods followed were those recommended by the International Streptomyces Project (ISP) for the characterization of Streptomyces species [E. B. Shirling and D. Gottlieb, "Methods for Characterization of Streptomyces species," *Int. J. Syst. Bacteriol.* 16: 313–340 (1966)] and those recommended for the characterization of Nocardia species by Gordon, Barnett, Handerhan and Pang, supra.

ISCC-NBS Centroid Color Charts, standard sample No. 2106 (National Bureau of Standards, 1958, U.S. Department of Commerce, Washington, D.C.) were used to assign color names to the reverse side and to aerial hyphae.

Morphology was studied using an optical light microscope and a scanning electron microscope (SEM).

The isomer of diaminopimelic acid (DAP) and the carbohydrates in hydrolysates of whole cells were established by the chromatographic methods of Becker et al. [B. Becker, M. P. Lechevalier, R. E. Gordon and H. E. Lechevalier, "Rapid Differentiation between Nocardia and Streptomyces by Paper Chromatography of Whole-cell Hydrolysates," *Appl. Microbiol.* 12, 421–423 (1964)] and of Lechevalier and Lechevalier [M. P. Lechevalier and H. Lechevalier, "Chemical Composition as a Criterion in the Classification of Aerobic Actinomycetes," *Int. J. Syst. Bacteriol.* 20, 435–443 (1970)].

Phospholipids were determined by the procedure of M. P. Lechevalier, et al. [M. P. Lechevalier, A. E. Stern, and H. A. Lechevalier, "Phospholipids in the taxonomy of Actinomycetes," *Actinomycetes, Zbl. Bakt. Suppl.* 11, K. P. Schaal and G. Pulverer (eds), Gustav Fischer Verlag, New York, 1981].

Menaquinone composition was determined by following the procedures of R. M. Kroppenstedt [in *Chemical Methods in Bacterial Systematics*, M. Goodfellow and D. E. Minnikin (eds), 1985, pp. 173–196] and M. D. Collins (ibid., pp. 267–285).

Resistance to antibiotics was measured by padding antibiotic sensitivity discs onto the surface of seeded ISP No. 2 agar plates.

Fatty acid analysis was done using the HP 5898A Microbial Identification System [see L. Miller and T. Berger, "Bacterial Identification by Gas Chromatography of Whole Cell Fatty Acids," Hewlett-Packard Application Note 228–41, 8pp. (1985)].

Fatty acid methyl esters were made from lyophilized whole cells grown under identical conditions.

Figure 3:
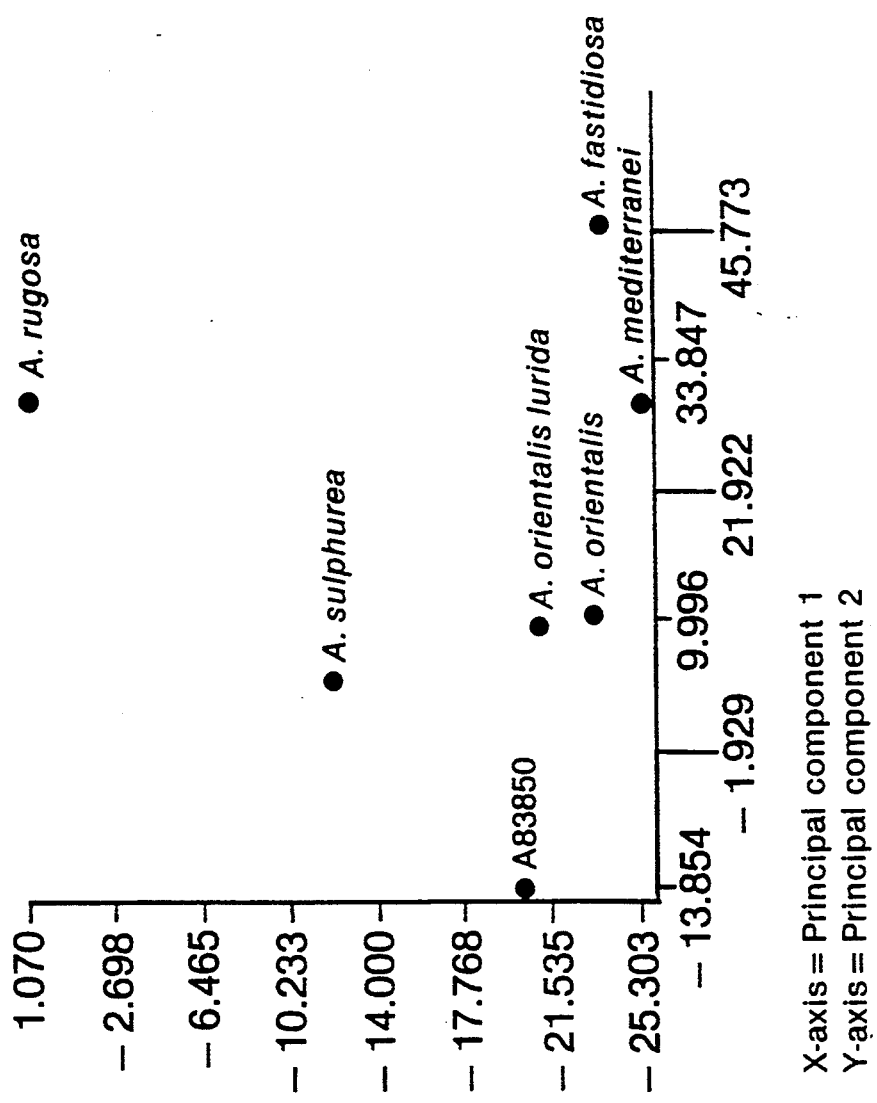
FIG. 3 is a principle component plot which compares the fatty acids present in culture A83850 with those of known Amycolatopsis species.

Principal component analysis was two dimensional and computer generated. Units of measurement in the principal component plot (shown in FIG. 3) indicate Euclidian distance.

Mycolic acids were determined by the methods proposed by Minnikin [D. E. Minnikin, I. G. Hutchinson and A. B. Caldicott, "Thin-Layer Chromatography of Methanolysates of Mycolic Acid-Containing Bacteria," *J. Chromatography* 188, 221–233 (1980)].

Cultural Characteristics

Culture A83850 grew well on both complex and defined media. The culture produced aerial mycelia on most of the media used. The aerial spore-mass color was white.

The reverse side was yellow-brown. No distinctive pigmentation was present. A soluble faint light brown pigment was released into the medium in some media.

The cultural characteristics are summarized in Table III.

TABLE III

Cultural Characteristics of A83850*

| Medium | Growth | Reverse Color | Aerial Growth | Mycelium Color | Soluble Pigment |
|---|---|---|---|---|---|
| ISP medium 2 | Abundant | 54.brO | Abundant | 263.White | 1.Brown |
| ISP medium 3 | Fair | 90.gy.Y | Fair | 263.White | None |
| ISP medium 4 | Good | 55.s Br | Good | 263.White | None |
| ISP medium 5 | Abundant | 76.l.yBr | Abundant | 263.White | None |
| AIA Agar[1] | Abundant | 71.m.OY | Abundant | 263.White | 1.Brown |
| ATCC No. 172 | Good | 89.p. Y | Good | 263.White | None |
| Bennetts | Abundant | 76.l.yBr | Abundant | 263.White | None |
| Calcium-malate | Abundant | 89.p Y | Abundant | 263.White | None |
| Chitin | Fair | 93.y Gray | Poor | 263.White | None |
| Czapeks | Good | 70.l. OY | Abundant | 263.White | None |
| Emerson | Abundant | 72.d. OY | Good | 263.White | 1.Brown |
| Glu.—Asp.[2] | Abundant | 70.l.OY | Poor | 263.White | None |
| Gly.—Gly.[3] | Abundant | 77.m.yBr | Abundant | 264.l.Gray | None |
| Nutrient | Good | 70.l.OY | Fair | 263.White | 1.Yellow |
| TPO[4] | Abundant | 77.m.yBr | Abundant | 263.White | None |
| Tap Water Agar | Fair | 93.y Gray | Poor | 263.White | None |
| YDA[5] | Good | 76.l.yBr | None | — | 1.Brown |

[1]Actinomycete Isolation Agar, Difco
[2]Glucose Asparagine Agar
[3]Glycerol Glycine Agar
[4]Tomato Past Oatmeal Agar
[5]Yeast Dextrose Agar
*Incubated for 21 days at 30° C.

Morphological Characteristics

Culture A83850 produced an extensive substrate mycelium that fragmented in liquid fermentation. No fragmentation was observed when the culture was grown on agar media.

Circular colonies, 5–7 mm in diameter, having a wrinkled surface covered with fine white aerial hyphae, with raised center and yellow-brown reverse color, were observed when the culture was plated on ISP medium 2.

Aerial hyphae were present on most of the media. The aerial hyphae were segmented into long strands of conidia and arranged in typical cobweb morphology characteristic of the nonstreptomycete actinomycetes [see S. A. Waksman, *The Actinomycetes*, Vol. 2, The Williams & Wilkins Co., Baltimore, 1961].

The conidia were cylindrical in shape with a smooth surface and averaged 1.3×0.4 mm in size. No sporangia or motile cells were observed.

Physiological Characteristics

Culture A83850 produced acid from the following carbohydrates: D-arabinose, D-fructose, D-glucose, glycerol, D-mannose, D-ribose and trehalose.

The culture did not produce acid from: cellulose, dulcitol, ethanol, glycogen, inulin, D-melezitose, sorbitol, L-eorbose, or xylitol.

The following carbohydrates were utilized with ISP medium 9 as the basal medium: D-fructose, D-galactose, D-glucose, inositol, D-mannitol, D-raffinose, salicin and D-xylose. L-arabinose, L-rhamnose, and sucrose were not utilized.

Culture A83850 used the following organic acids as sodium salts: acetate, butyrate, formate, lactate, malate, propionate, pyruvate and succinate. The culture did not use mucate, oxalate or tartrate.

Culture A83850 hydrolyzed allantoin, calcium malate, casein, elastin, hippurate, and L-tyrosin. Culture A83850 was unable to hydrolyse adenine or guanine. The culture hydrolyzed testosterone to a slight extent.

Culture A83850 produced catalase, esculinase, gelatinase, and $H_2S$. It did not produce melanoid pigments. It hydrolyzed but did not peptonize skim milk. It was unable to survive at 50° C. for 8 hours, but grew at temperatures between 15° C. and 37° C.

Culture A83850 was resistant to bacitracin (10 units), neomycin (30 μg), oleandomycin (15 μg), rifampin (5 μg) and tetracycline (30 μg). It was inhibited by cephalothin (30 μg), gentamicin (10 μg), lincomycin (2 μg), penicillin (10 units), streptomycin (10 μg), tobramycin (10 μg), and vancomycin (30 μg).

Cell-Wall Analysis

Hydrolyzed whole cells of A83850 contained meso-diaminopimelic acid. Diagnostic sugars in the whole-cell extracts were galactose and arabinose. Thus, A83850 has a Type IV cell-wall pattern and a Type A sugar pattern (Lechevalier and Lechevalier, supra). The cells do not contain mycolic acids.

Phospholipid determinations on the whole cells indicated the presence of phosphatidyl ethanolamine, phosphatidyl glycerol and physphatidyl inositol. Thus, A83850 has a Type PII phospholipid pattern (Lechevalier, Stern and Lechevalier, supra).

The major menaquinone detected was $MK-9(H_4)$. A minor amount of $MK-8(H_4)$ Was observed.

Phage Plating

Two broad-host-range Streptomyces bacteriophage and six Amycolatopsis bacteriophage were tested for their ability to form plaques on A83850. The two Streptomyces bacteriophage and one of the Amycolatopsis bacteriophage did not form plaques on A83850. The remaining five Amycolatopsis bacteriophage did not form plaques on A83850, but demonstrated lysis from without at high multiplicities of bacteriophage. This killing from without suggests that A83850 is possibly related to Amycolatopsis.

Identity of A83850

Culture A83850 is a nocardioform strain with a Type IV cell wall, Type A whole cell sugar pattern, Type PII phospholipid pattern, and no mycolates. These chemotaxonomic characteristics plus the cultural and morphological properties place A83850 in the genus Amycolatopsis. At present there are six species and one subspecies in this genus: *A. azurea, A. fastidiosa, A. mediterranei, A. orientalis, A. orientalis* subsp. *lurida, A. rugosa,* and *A. sulphurea.*

Biochemical similarity was measured by constructing a table of similarity coefficients based on biochemical measurements taken from the literature [see A. Henssen et al., supra, and Lechevalier, Prauser, Labeda, and Ruan, supra. The coefficient of Jaccard Sj and the simple matching coefficient $S_{sm}$ were used [see W. Kurylowicz et al., supra, p. 37].

Table IV summarizes these similarity coefficients.

TABLE IV

| Similarity Coefficients for A83850 and Amycolatopsis Species | | |
|---|---|---|
| Culture | $S_{sm}$ | Sj |
| A83850 | 100 | 100 |
| A. orientalis | 80 | 74 |
| A. orientalis subsp. lurida | 80 | 73 |

TABLE IV-continued

| Similarity Coefficients for A83850 and Amycolatopsis Species | | |
|---|---|---|
| Culture | $S_{sm}$ | Sj |
| A. mediterranei | 74 | 63 |
| A. azurea | 67 | 63 |
| A. rugosa | 55 | 42 |
| A. sulphurea | 55 | 39 |
| A. fastidiosa | 32 | 19 |

Fatty acid analysis was performed on A83850 and the available Amycolatopsis strains. A comparison of the percentage of fatty acids is given in Table V. There is considerable variation of A83850 from the other species in the amount of 14:0 ISO, 15:0 ISO, 15:0 Anteiso, 16:0 ISO, 17:1 C and 17:0 fatty acids.

TABLE V

| Fatty Acid | Percentage fatty acid composition of A83850 and Amycolatopsis strains | | | | | | |
|---|---|---|---|---|---|---|---|
| | A83850 | A. orientalis | A. lurida | A. fastidiosa | A. rugosa | A. mediterr. | A. sulphur. |
| 14:0 Iso | 2.85 | 9.52 | 6.82 | 3.09 | — | 1.20 | 3.68 |
| 15:0 Iso | 29.97 | 12.39 | 14.45 | 7.21 | 1.14 | 9.27 | 9.28 |
| 15:0 Anteiso | 6.64 | 1.74 | 2.24 | — | — | 1.35 | 4.95 |
| 15:1 B[6] | 1.28 | — | — | 0.72 | 1.59 | 1.99 | — |
| 15:0 | 6.02 | 4.69 | 5.85 | 0.73 | 1.18 | 3.09 | 3.35 |
| 16:1 Iso H | — | — | — | 11.09 | 17.88 | 2.25 | — |
| 16:0 Iso | 9.27 | 30.14 | 27.87 | 56.70 | 29.91 | 44.86 | 21.01 |
| 16:0 | 7.84 | 7.60 | 5.29 | 0.56 | 3.39 | 0.97 | 17.12 |
| 16:1 Cis 9 | — | — | 3.07 | 1.34 | 10.42 | 1.25 | 3.85 |
| 17:1 Iso G | — | — | — | — | 3.06 | 1.50 | — |
| 17:0 Iso | 2.75 | 1.43 | 1.30 | 1.29 | 2.56 | 2.70 | 2.01 |
| 17:0 Anteiso | 3.77 | 1.37 | 1.67 | 0.80 | 3.34 | 4.04 | 5.56 |
| 17:1 B | 4.18 | 4.25 | 7.79 | 0.65 | 4.83 | 6.13 | 1.84 |
| 17:1 C | 0.90 | 5.06 | 6.16 | 15.81 | 18.07 | 8.95 | 7.03 |
| 17:0 | 18.58 | 12.84 | 10.95 | — | 1.10 | 2.86 | 9.34 |
| 18:1 Iso F | — | 1.28 | 0.85 | — | — | 5.60 | — |
| 18:1 Cis 9 | — | — | — | — | 1.43 | — | — |
| 18:0 Iso | — | 1.13 | — | — | — | — | — |
| 18:0 | 1.47 | 1.72 | 1.48 | — | — | — | 3.21 |

[6]B, C, F, G, and H, indicate double bond position/configurations that are unknown.

Principal component analysis of the fatty acid compositions shown in Table III show sufficient scattering to suggest the cultures are all distinct species within the same genus. The principal component plot is presented in FIG. 3.

Figure 4:
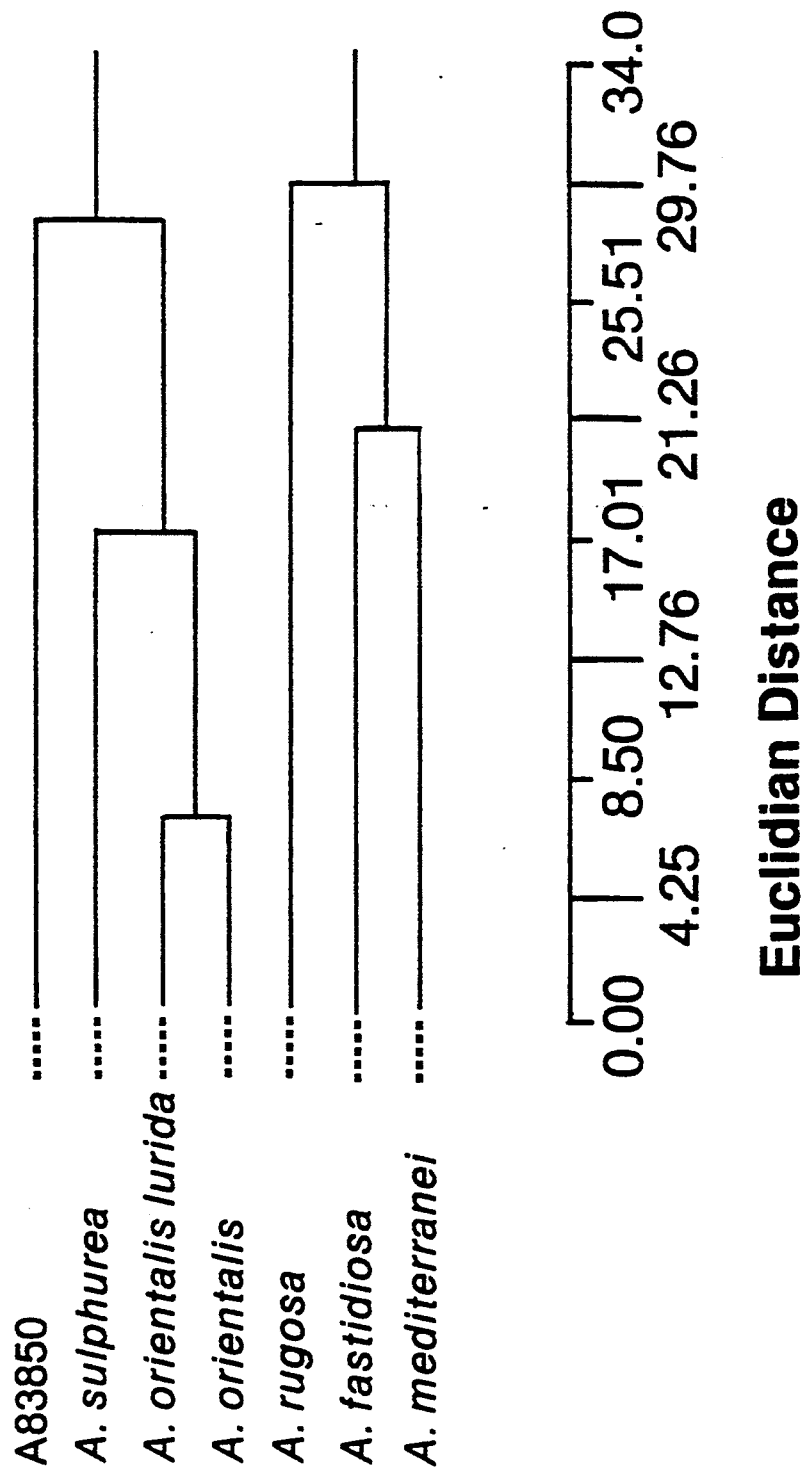
FIG. 4 is a dendogram which shows the relationship of A83850 to the other Amycolatopsis species based on Euclidian distance.

A dendogram is presented in FIG. 4, which shows the relationship of A83850 to the other Amycolatopsis species based on Euclidian distance. This data also suggests that A83850 is a distinct species.

Table VI compares the differential characteristics of A83850 to those of the existing Amycolatopsis species and subspecies.

TABLE VI

| Characteristic | Differential characteristics of A83850 and Amycolatopsis species | | | | | | | |
|---|---|---|---|---|---|---|---|---|
| | A83850 | A. orientalis | A. lurida | A. fastidiosa | A. rugosa | A. mediterr. | A. sulphur. | A. azurea |
| Decomposition of: | | | | | | | | |
| Hypoxanthine | + | + | + | − | + | + | + | − |
| Xanthine | + | + | + | − | + | − | − | − |
| Decarboxylation of: | | | | | | | | |
| Benzoate | − | − | − | − | + | − | − | − |
| Citrate | + | + | + | + | − | + | + | + |
| Production of: | | | | | | | | |
| Nitrate reductase | − | + | + | + | − | + | + | + |
| Amylase | + | − | − | ND | − | − | − | ND |
| Urease | + | + | + | ND | + | + | − | ND |
| Phosphatase | + | + | − | ND | + | + | + | ND |
| Resistant to: | | | | | | | | |
| Lysozyme broth | + | − | − | ND | − | + | + | ND |
| 5% NaCl | + | + | V[7] | + | + | − | + | + |
| Growth at: | | | | | | | | |
| 10° C. | − | + | + | + | + | + | − | + |

TABLE VI-continued

Differential characteristics of A83850 and Amycolatopsis species

| Characteristic | A83850 | A. orientalis | A. lurida | A. fastidiosa | A. rugosa | A. mediterr. | A. sulphur. | A. azurea |
|---|---|---|---|---|---|---|---|---|
| 45° C. | − | − | − | ND | + | − | − | ND |
| Aerial mycelium (AM) | + | + | + | + | − | + | + | + |
| Color of AM: | | | | | | | | |
| White | + | + | + | + | − | + | + | + |
| Yellowish green | − | − | − | − | − | − | + | − |
| Pink | − | − | − | + | − | − | − | + |
| Blue | − | − | − | − | − | − | − | + |
| Soluble Pigment (SP | − | − | − | + | + | − | − | + |
| Color of SP: | | | | | | | | |
| Yellow | − | − | − | + | − | − | − | − |
| Brown | − | − | − | + | + | − | − | − |
| Blue | − | − | − | − | − | − | − | + |
| Acid produced from: | | | | | | | | |
| Adonitol | + | + | + | − | + | − | − | + |
| L-Arabinose | + | + | + | − | + | + | − | + |
| Cellobiose | + | + | + | − | − | + | − | + |
| Dextrin | − | + | + | ND | − | + | + | ND |
| meso-Erythritol | + | + | + | − | + | − | − | + |
| D-Galactose | + | + | + | − | + | + | + | + |
| Inositol | + | + | + | − | − | + | + | + |
| Lactose | + | + | + | − | − | + | + | + |
| Maltose | + | + | + | ND | − | + | + | ND |
| D-Mannitol | + | + | + | − | + | + | + | + |
| Melibiose | + | + | − | ND | − | + | − | ND |
| α-Me-D-glucoside | + | + | + | ND | − | + | − | ND |
| Raffinose | + | − | − | − | − | + | − | + |
| L-Rhamnose | − | + | − | − | + | + | − | + |
| Salicin | + | + | + | ND | + | + | − | ND |
| Sucrose | − | + | + | − | − | + | + | + |
| D-Xylose | + | + | + | ND | + | + | − | ND |

*aV = variable results*
ND = not done

Culture A83850 appears quite similar to both *A. orientalis*, and *A. orientalis* subsp. *lurida*, however when fatty acid measurements are factored into the evaluation, the differences become too great to consider A83850 synonymous. Therefore the data indicates that A83850 is a new strain belonging to the genus Amycolatopsis for which the name *Amycolatopsis albus* has been selected. The name albus refers to the white color of the culture.

As is the case with other organisms, the characteristics of the A83850-producing culture of this invention, *Amycolatopsis albus* NRRL 18532, continue to be subject to variation. Thus, mutants of this strain may be obtained by physical and chemical methods known in the art. For example, other strains can be obtained by treatment with chemicals such as N-methyl-N'-nitro-N-nitrosoguanidine. Natural and induced mutants of the *Amycolatopsis albus* strain NRRL 18532 which retain the characteristic of producing a recoverable amount of A83850 are part of this invention.

The culture medium used to grow the *Amycolatopsis albus* cultures can be any one of a number of media. For economy in production, optimal yield, and ease of product isolation, however, certain culture media are preferred. Thus, for example, preferred carbohydrate sources in large-scale fermentation are glucose and potato dextrin, although ribose, xylose, fructose, galactose, mannose, mannitol, soluble starch and the like can also be used.

Preferred nitrogen sources are enzyme-hydrolyzed casein and meat peptones, although yeast extract, acid-hydrolyzed casein, beef extract, fish meal, liver meal, and the like can also be used.

Among the nutrient inorganic salts which can be incorporated in the culture media are the customary soluble salts capable of yielding zinc, sodium, magnesium, calcium, ammonium, chloride, carbonate, sulfate, nitrate and like ions.

Essential trace elements necessary for the growth and development of the organism should also be included in the culture medium. Such trace elements commonly occur as impurities in other substituents of the medium in amounts sufficient to meet the growth requirements of the organism.

If foaming is a problem, small amounts (i.e. 0.2 ml/L) of an antifoam agent such as polypropylene glycol may be added to large scale fermentation media.

For production of substantial quantities of the A83850 antibiotics, submerged aerobic fermentation in tanks is preferred. Small quantities of the antibiotics may be obtained by shake-flask culture. Because of the time lag in antibiotic production commonly associated with inoculation of large tanks with the spore form of the organism, it is preferable to use a vegetative inoculum. The vegetative inoculum is prepared by inoculating a small volume of culture medium with the spore form or mycelial fragments of the organism to obtain a fresh, actively growing culture of the organism. The vegetative inoculum is then transferred to a larger tank. The vegetative inoculum medium can be the same as that used for larger fermentations, but other media are also suitable.

The A83850 antibiotics are produced by the A83850-producing organisms when grown at temperatures between about 23° and about 37° C. Optimum temperature for A83850 production appears to be about 30° C.

As is customary in submerged aerobic culture processes, sterile air is blown into the vessel from the bottom while the medium is stirred with conventional turbine impellors. The maximum oxygen uptake of the fermentation under the conditions used thus far has not exceeded about 0.2 mM/L/minute. In general, the aeration rate and agitation rate should be sufficient to maintain the level of dissolved oxygen at or above 50% of saturation.

Production of the A83850 antibiotics can be followed during the fermentation by testing samples of the broth for antibiotic activity against organisms known to be sensitive to the antibiotic. Useful assay organisms are *Staphylococcus aureus* and *Bacillus subtilis* ATCC 6633. The bioassays are conveniently performed by the agar-well plate test.

Following their production under submerged aerobic fermentation conditions, the A83850 antibiotics can be recovered from the fermentation medium by methods used in the art. Recovery of A83850 is accomplished by filtering the medium to separate the broth from the mycelial mass.

A83850 can be recovered from the filtered broth by a variety of techniques. A preferred technique involves adjusting the filtered broth to a pH of about 6-7 and adsorbing it onto a cation exchange resin, e.g. Dowex XF5-43278, Dowex-50 or Amberlite IR-120. The active material is eluted from the resin with a suitable solvent such as dilute $NH_4OH$ solution. The fractions can be monitored for activity by bioassay using *Bacillus subtilis*.

If desired, the crude A83850 can be further separated into individual components A834850A and A83850B. In one method, the A83850 is adsorbed on a reverse-phase silica-gel ($C_{18}$ or $C_8$), and eluted with a suitable solvent such as stepwise elution with acetonitrile:0.25% triethylamine (TEA), pH 3.0 (7.5:92.5) and $CH_3CN$:0.25% TEA, pH 3.0 (9.5:90.5). The elution can be monitored by bioassay or by UV at 225 nm.

To obtain A83850A and A83850B of even greater purity, the products can be further separated by adsorbing them onto a cation exchange resin, e.g. Dowex XF5-43278, Dowex-50 or Amberlite IR-120, and eluting with a gradient such as 10% MeOH/0.15M $NaH_2PO_4$ to 10% MeOH/0.4M $NaH_2PO_4$.

Alternatively, the culture solids, including medium constituents and mycelium can be used without extraction or separation, but preferably after removal of water, as a source of A83850. For example, after production of A83850, the whole fermentation broth can be dried by lyophilization, by drum-drying, or by azeotropic distillation and drying. The dried broth is then mixed directly into feed premix.

The minimal inhibitory concentrations (MIC's) at which the A83850 antibiotics inhibit certain bacteria are given in Tables VII. The MIC's in Table VII were determined by standard agar-dilution assays.

TABLE VII

In Vitro Antibacterial Activity of the A83850 Antibiotics and Vancomycin

| Test Organism | MIC (mcg/mL) | | | | |
| --- | --- | --- | --- | --- | --- |
| | A83850A | Reduced A83850A | A83850B | Reduced A83850B | Vancomycin |
| *Staphylococcus aureus* Xi.1 | 1.0 | 2.0 | 0.5 | 1.0 | 0.5 |
| *Staphylococcus aureus* V41 | 2.0 | 2.0 | 1.0 | 1.0 | 0.5 |
| *Staphylococcus aureus* X400 | 2.0 | 2.0 | 1.0 | 1.0 | 1.0 |
| *Staphylococcus aureus* S13E | 2.0 | 2.0 | 0.5 | 1.0 | 0.5 |
| *Staphylococcus epidermidis* 270 | 4.0 | 4.0 | 1.0 | 2.0 | 1.0 |
| *Staphylococcus epidermidis* 222 | 2.0 | 4.0 | 1.0 | 2.0 | 1.0 |
| *Streptococcus pyogenes* C203 | 1.0 | 2.0 | 0.5 | 0.5 | 0.5 |
| *Streptococcus pneumoniae* Park 1 | 1.0 | 0.25 | 0.125 | 0.125 | 0.5 |
| *Enterococcus faecium* X66 | 2.0 | 2.0 | 1.0 | 1.0 | 1.0 |
| *Enterococcus faecalis* 2041 | 8.0 | 8.0 | 4.0 | 4.0 | 4.0 |

One important aspect of the antimicrobial activity of A83850 compounds is their activity against anaerobic bacteria. This activity is illustrated in Table VIII, which summarizes the activity of A83850A and A82846B against various anaerobic bacteria, as determined by standard agar-dilution assay. End points were read after 24-hour incubation.

TABLE VIII

Activity of A83850A and B Against Anaerobic Bacteria

| Anaerobic Bacteria | MIC (mcg/mL) | | |
| --- | --- | --- | --- |
| | A83850A | A83850B | Vancomycin |
| Gram-positve Strains: | | | |
| *Clostridium difficile* | 4 | 2 | 2 |
| *Clostridium perfringens* | 2 | 2 | 2 |
| *Clostridium septicum* | 2 | 1.0 | 2 |
| *Eubacterium aerofaciens* | 2 | 2 | 8 |
| *Peptococcus asaccharolyticus* | 16 | 2 | 4 |
| *Peptococcus prevoti* | 16 | 2 | 4 |
| *Peptostreptococcus anaerobius* | 32 | 16 | 1.0 |
| *Peptostreptococcus intermedius* | 2.0 | 2.0 | 2.0 |
| *Propionibacterium acnes* | 8.0 | 8.0 | 4.0 |
| Gram-negative Strains: | | | |
| *Bacteroides fragilis* | 16.0–32.0 | 16.0–32.0 | 16.0–32.0 |
| *Bacteroides thetaiotaomicron* | 64 | 64 | 64 |
| *Bacteroides melaninogenicus* | 16 | 32 | 128 |
| *Bacteroides vulgatis* | 16 | 16 | 16 |
| *Bacteroides corrodens* | 32 | 32 | 32 |
| *Fusobacterium symbiosum* | 4 | 2 | 2 |
| *Fusobacterium necrophorum* | 1.0 | 1.0 | 1.0 |

The A83850 antibiotics have also shown in vivo antimicrobial activity against experimentally-induced infections in laboratory animals. When two doses of test compound were administered to mice experimentally infected with the test organism, the activity observed was measured as an $ED_{50}$ value [effective dose in mg/kg to protect 50% of the test animals: see Warren Wick, et al., *J. Bacteriol.* 81, 233–235 (1961)]. $ED_{50}$ values observed for illustrative compounds are given in Table IX.

TABLE IX

In Vivo Activity of A83850 Antibiotics

| Compound | $ED_{50}$ Value[a] | | |
| --- | --- | --- | --- |
| | *Staphylococcus aureus* | *Streptococcus pyogenes* | *Streptococcus pneumoniae* |
| A83850A | 2.87 | 3.62 | 2.73 |
| Reduced A83850A | 7.10 | 2.30 | 3.88 |
| A83850B | 2.87 | 2.19 | 0.98 |
| Reduced A83850B | 2.12 | 1.36 | 1.99 |
| Vancomycin | 1.43 | 0.98 | 0.67 |

[a]mg/kg × 2; doses administered subcutaneously to mice 1 and 4 hours post-infection Pharmaceutical formulations of the A83850 antibiotics are also part of this invention. Thus, the antibiotic, preferably in the form of a pharmaceutically acceptable salt, can be formulated for oral or parenteral administration for the therapeutic or prophylactic treatment of bacterial infections. For example, the compound can be admixed with conventional pharmaceutical carriers and excipients and used in the form of tablets, capsules, elixirs, suspensions, syrups, wafers and the like. The A83850 compositions will contain from about 0.1 to about 90% by weight of the active compound, and more generally from about 10 to about 30%.

The compositions may contain common carriers and excipients, such as corn starch or gelatin, lactose, sucrose, microcrystalline cellulose, kaolin, mannitol, dicalcium phosphate, sodium chloride and alginic acid.

Disintegrators commonly used in the formulations of this invention include croscarmellose sodium, microcrystalline cellulose, corn starch, sodium starch glycolate and alginic acid.

Tablet binders that can be included are acacia, methylcellulose, sodium carboxymethylcellulose, polyvinylpyrrolidone (Povidone), hydroxypropyl methylcellulose, sucrose, starch and ethylcellulose.

Lubricants that can be used include magnesium stearate or other metallic stearates, stearic acid, silicone fluid, talc, waxes, oils and colloidal silica.

Flavoring agents such as peppermint, oil of wintergreen, cherry flavoring or the like can also be used. It may be desirable to add a coloring agent to make the dosage form more esthetic in appearance or to help identify the product.

For intravenous(IV) use, a water soluble form of the antibiotic can be dissolved in one of the commonly used intravenous fluids and administered by infusion. Such fluids as, for example, physiological saline, Ringer's solution or 5% dextrose solution can be used.

For intramuscular preparations, a sterile formulation of a suitable soluble salt form of the compound, for example the hydrochloride salt, can be dissolved and administered in a pharmaceutical diluent such as Water-for-Injection, physiological saline or 5% glucose solution. A suitable insoluble form of the compound may be prepared and administered as a suspension in an aqueous base or a pharmaceutically acceptable oil base, e.g. an ester of a long chain fatty acid such as ethyl oleate.

For oral use, a sterile formulation of a suitable salt form of the antibiotic, for example, the hydrochloride salt, formulated in a diluent such as distilled or deionized water, is particularly useful.

Alternatively, the unit dosage form of the antibiotic can be a solution of the antibiotic, preferably in its salt form, in a suitable diluent in sterile, hermetically sealed ampoules. The concentration of the antibiotic in the unit dosage may vary, e.g. from about 1 percent to about 50 percent depending on the particular form of the antibiotic and its solubility and the dose desired by the physician.

In a further aspect, this invention provides a method for treating infectious diseases, especially those caused by Gram-positive microorganisms, in animals. The animal may be either susceptible to, or infected with, the microorganism. The method comprises administering to the animal an amount of an A83850 antibiotic which is effective for this purpose. In general, an effective amount of A83850 antibiotic is a dose between about 0.5 and about 150 mg/kg. A preferred dose is from about 1 to about 100 mg/kg of active compound. A typical daily dose for an adult human is from about 50 mg to about 1.0 g.

In practicing this method, the antibiotic can be administered in a single daily dose or in multiple doses per day. The treatment regime may require administration over extended periods of time, e.g., for several days or for from one to six weeks. The amount per administered dose or the total amount administered will depend on such factors as the nature and severity of the infection, the age and general health of the patient, the tolerance of the patient to the antibiotic and the microorganism or microorganisms involved in the infection.

A convenient method of practicing the treatment method is to administer the antibiotic via IV infusion. In this procedure a sterile formulation of a suitable soluble salt of the antibiotic is incorporated in a physiological fluid, such as 5% dextrose solution, and the resulting solution is infused slowly IV. Alternatively, the piggyback method of IV infusion can also be used.

In other embodiments, this invention relates to 1) methods and compositions for increasing feed-utilization efficiency in animals such as poultry, swine, sheep and cattle, 2) methods and compositions for promoting growth in animals such as poultry, swine, sheep and cattle raised for meat production and 3) methods and compositions for enhancing milk production in lactating ruminants.

For increasing feed-utilization efficiency and promoting growth, an A83850 antibiotic is administered orally in a suitable feed in an amount of from about 2 to about 200 grams per ton of total feed. For beef cattle, for example, a range of about 12 to 3000 mg/head/day is suitable.

For enhancing milk production in lactating ruminants, oral administration of a daily amount of from about 0.04 to about 16 mg/kg of body weight (or about 25 to about 5000 mg/animal/day) in a suitable feed is suggested.

In order to illustrate more fully the operation of this invention, the following examples are provided:

EXAMPLE 1

A83850 HPLC Assay Method

The following analytical HPLC system is useful for the A83850 components:

1. Cation Exchange Resin Column
Column Support: Zorbax* SCX(4.5×150 mm)
System: Gradient Elution A:B (1:0) to A:B (0:1) in 5 min., hold for 5 min.
A=MeOH:0.15M $NaH_2PO_4$ (1:9)
B=MeOH:0.8M $NaH_2PO_4$ (1:9)
Flow Rate: 1.5 mL/min
Detection: UV at 225 nm
Retention Times: are concentration dependent, but are approximately:
A83850B=2.65 min
A83850A=4.45 min

*Zorbax columns are products of E. I. dupont de Nemours & Co., Inc., Wilmington, Del. 19898

EXAMPLE 2

Preparation of Antibiotic A83850 Using Culture A83850

A. Shake-flask Fermentation of Culture A83850

The culture *Amycolatopsis albus* NRRL 18532, either as a lyophilized pellet or as a suspension maintained in liquid nitrogen, is used to inoculate a seed medium having the following composition:

| VEGATATIVE MEDIUM | |
| --- | --- |
| Ingredient | Amount (%) |
| Glucose | 2.0 |
| Soluble starch | 2.0 |
| Yeast extract | 0.5 |
| Enzymatic hydrolysate of casein* | 0.5 |
| CaCO₃ | 0.1 |
| Deionized water | q.s. 1 liter |

Adjust the pH of the medium to about 7.2 with NAOH before sterilizing.
*NZ Amine A, Sheffield Chemical Co., Norwich, NY Slants or plates are prepared by adding 2.5% agar to the seed medium. The inoculated slant is incubated at 30° C. for from about 10 to about 14 days. The mature slant culture is scraped with a sterile tool to loosen the spores and remove and mascerate the mycelial mat. About one-fourth of the loosened spores and culture growth thus obtained is used to inoculate 50 mL of a first-stage seed medium.

The inoculated first-stage medium is incubated in a 250-mL Erlenmeyer flask at 30° C. for about 24-48 hours on a shaker orbiting in a two-inch (5.08 cm) circle at 250 rpm.

This incubated first-stage medium (0.5 mL) is used to inoculate 50 mL of a production medium having the following composition:

| Ingredient | Amount (%) |
| --- | --- |
| Glucose | 2.0 |
| Meat Peptone | 0.1 |
| Potato dextrin | 4.0 |
| CaCO₃ | 0.5 |
| NaNO₃ | 0.75 |
| KCl | 0.5 |
| MgSO₄.7H₂O | 0.1 |
| Mineral Stock[1] | 1.0 |
| Deionized water | q.s. 1 liter |

(Presterilization pH adjusted to 7.0 with NAOH)

a. Bacto Peptone, Difco Laboratories
b. 10 mL of Mineral Stock contains:

| FeSO₄.7H₂O | 0.003 g |
| --- | --- |
| CuSO₄.5H₂O | 0.003 g |
| ZnSO₄.7H₂O | 0.003 g |
| MnSO₄.H₂O | 0.0007 g |

The inoculated production medium is incubated in a 250-mL wide-mouth Erlenmeyer flask at 30° C. for 4 to 5 days on a shaker orbiting in a two-inch circle at 250 rpm.

B. Tank Fermentation of Culture A83850

In order to provide a larger volume of inoculum, 400 mL of incubated first-stage medium, prepared as described in Section A, is used to inoculate 400 mL of a second-stage growth medium having the same composition as that of the first-stage medium. This second-stage vegetative medium is incubated in a 2-L wide-mouth Erlenmeyer flask for about 48 hours at 30° C. on a shaker orbiting in a two-inch circle at 250 rpm.

Incubated second-stage vegetative medium (2L) thus prepared is used to inoculate 110 liters of sterile production medium, prepared as described in Section A except that antifoams (P-2000 0.1 mL/L and Sag 471, 0.2 mL/L) are added. The inoculated production medium is allowed to ferment in a 165-L stirred fermentation tank for 100 to 120 hours at a temperature of 30° C. The airflow in the stirred vessel is adjusted to maintain a dissolved oxygen level above 50% of air saturation.

EXAMPLE 3

Preparation of Crude A83850

Fermentation broth (220 L) prepared as described in Example 2, Section B, was filtered through a filter press using a filter aid (3% Hyflo Supercel). The filtrate (190 L) was adjusted to pH 6.4 and applied to a column of Dowex-XFS-43278 ($NH_{4+}$) resin.

The column was washed with 100 L $H_2O$. The active material was eluted from the resin with 5 column volumes of 0.05N $NH_4OH$, collecting 4-L fractions. Fractions were assayed by bioassay using *Bacillus subtilis*. Fractions containing A83850 were combined, concentrated in vacuo, and freeze-dried to yield 22 g of crude A83850.

EXAMPLE 4

Separation of A83850A and A83850B

A83850 (30 g), prepared as described in Example 3, was dissolved in water (400 mL), adjusted to pH 9.5, and loaded onto a Chromatospac column containing 4.5 L of silica gel/$C_{18}$. The column was developed stepwise with 4 L of acetonitrile:0.25% TEA, adjusted to pH 3.0 with $H_3PO_4$ (7.5:92.5), and 10 L of $CH_3CN$:0.25% TEA, pH 3.0 (9.5:90.5). Fractions of 480 mL were collected and elution was monitored by bioassay and by UV at 225 nm. Bioactive fractions were assayed by analytical PIPLC, and fractions were combined dependent on factor content. Fractions 29-32 contained A83850B. Fractions 33-35 contained a mixture of A838-50A and A83850B. Fractions 36-56 contained A838-50A.

Combined fractions were adjusted to pH 6.4 with 5N NaOH and applied to a 200-mL column of Diaion HP-20 resin in $H_2O$. The column was washed with 1 L of water and eluted with 1 L each of 10%, 15%, and 20% aqueous $CH_3CN$, collecting 200-mL fractions. Bioactive fractions were combined, concentrated in vacuo and freeze-dried.

Less pure preparations such as the mixture of A838-50A and A83850B were purified on a Waters Prep 600 unit with Dupont Zorbax SCX resin, developing with a gradient from 10% aqueous MeOH/0.15M $NaH_2PO_4$ to 10% aqueous MeOH/0.8M $NaH_2PO_4$. The fractions containing the individual factors were desalted on HP-20 resin and freeze-dried to yield pure A83850A and A83850B.

EXAMPLE 5

Reduction of A83850A and A83850B

A mixture of approximately 85% A83850A and 15% A83850B was reduced. DMF (25 mL) was used to dissolve 329 mg of the mixture. Excess sodium cyanoborohydride (2.3 gm) was added. The reaction mixture was stirred at room temperature for 6 hours, concentrated in vacuo, and lyophilized.

The recovered material was desalted through HP20 resin (3.5 cm×35 cm column) and eluted with a stepwise gradient of 1.5 L each of water, 10% aqueous acetonitrile and 20% aqueous acetonitrile. The eluates were monitored by HPLC and appropriate fractions were pooled. Pooled fractions containing product were further purified by HPLC using a Waters Bondapak $C_{18}$ column (19×150 mm) eluted with a 20 minute linear gradient of 0.5% pyridinium acetate to 20% acetonitrile/0.5% pyridinium acetate and monitored by UV at 280 nm. Purification yielded 46.6 mg of reduced A838-50A and 7 mg of reduced A83850B.

EXAMPLE 6

Preparation of A83850 Salts

The A83850 component (100 mg) is dissolved in deionized water (10 mL). The pH of this solution is adjusted to about pH 3, using 0.5N acid (e.g. $H_2SO_4$ and $H_3PO_4$). The solution is lyophilized to give the appropriate salt form. It is important to note that if the pH is lowered to much below pH 3 (i.e. pH 2), the component is degraded.

EXAMPLE 7

A83850 Tablet Formulation

Tablets containing A83850 can be prepared using the following ingredients and amounts:

| Ingredient | Weight |
|---|---|
| A83850 phosphate | 282.9 mg |
| Microcrystalline cellulose | 101.1 mg |
| Croscarmellose sodium | 12.0 mg |
| Providone | 12.0 mg |
| Magnesium stearate | 3.0 mg |
| Stearic acid | 4.0 mg |
| Purified water | 0.16 mL |

Add A83850 phosphate, a portion of the microcrystalline cellulose and a portion of the croscarmellose sodium to a suitable container and blend until homogenous. Prepare a solution of Povidone in water, and add the Povidone solution to the blended powders. Granulate the resulting mixture, size if necessary and dry. Add the remaining microcrystalline cellulose and croscarmellose sodium to the dried mixture and blend. Add magnesium stearate and stearic acid, and blend the mixture. Compress the resulting powder blend into tablets.

EXAMPLE 8

A83850 Capsule Formulation

Capsules containing A83850 can be prepared using the following ingredients and amounts:

| Ingredient | Weight |
|---|---|
| A83850 hydrochloride | 262.2 mg |
| Corn starch flowable powder | 137.7 mg |
| Silicone fluid 350 centistokes | 2.7 mg |
| Corn starch | 147.1 mg |

Blend A83850 hydrochloride, starch flowable powder, silicone fluid 350 centistokes and starch powder in a suitable mixer until homogeneous. Fill into appropriate size hard gelatin capsules.

EXAMPLE 9

A83850 Suspension Formulation

Prepare a sterile insoluble form of A83850 by crystallization or precipitation. Mill or screen to a particle size suitable for suspension. Suspend the A83850 in the following vehicle.

| Ingredient | Amount |
|---|---|
| Lecithin | 1% |
| Sodium citrate | 2% |
| Propylparaben | 0.015% |
| Water for Injection | q.s. to desired volume |

The suspension may be manufactured in bulk and filled into vials or may be prepared extemporaneously by adding the vehicle to the A83850 in the vial.

We claim:

1. A biologically pure culture of *Amycolatopsis albus* NRRL 18532 or an A83850-producing mutant thereof.

* * * * *

UNITED STATES PATENT AND TRADEMARK OFFICE
CERTIFICATE OF CORRECTION

PATENT NO.   : 5,391,492

DATED        : February 21, 1995

INVENTOR(S)  : Hamill *et al*.

It is certified that an error appears in the above-identified patent and that said Letters Patent is hereby corrected as shown below:

Column 2, line 34, "279 run" should read, -- 279 nm --.

Column 18, line 31, "analytical PIPLC" should read, -- analytical HPLC --.

Signed and Sealed this

Twelfth Day of September, 1995

Attest:

BRUCE LEHMAN

Attesting Officer

Commissioner of Patents and Trademarks